United States Patent [19]

Gerster

[11] Patent Number: 5,175,296

[45] Date of Patent: Dec. 29, 1992

[54] IMIDAZO[4,5-C]QUINOLIN-4-AMINES AND PROCESSES FOR THEIR PREPARATION

[75] Inventor: John F. Gerster, Woodbury, Minn.

[73] Assignee: Minnesota Mining and Manufacturing Company, St. Paul, Minn.

[21] Appl. No.: 663,110

[22] Filed: Mar. 1, 1991

[51] Int. Cl.$^5$ .................. C07D 471/04; C07D 413/06
[52] U.S. Cl. ..................... 546/82; 544/124; 552/1
[58] Field of Search ............... 546/82, 81; 544/124; 552/1

[56] References Cited

U.S. PATENT DOCUMENTS

| | | | |
|---|---|---|---|
| 4,689,338 | 8/1987 | Gerster | 514/293 |
| 4,929,624 | 5/1990 | Gerster et al. | 514/293 |
| 4,988,815 | 1/1991 | Andre et al. | 546/159 |

OTHER PUBLICATIONS

Chemical Abstracts, vol. 103 (No. 23), Abst. No. 196,090s Dec. 9, 1985.
Chemical Abstracts, vol. 108, (No. 9), Abst. No. 75,403-v Feb. 29, 1988.
Angewandte Chemie International Edition in English 1963,2, 565 (Huisgen, Oct. 1963).
Chem. Ber. 1989, 102,926 (Seidl et al.).
J. Pharm. Soc. Jap. 1966, 86, 576 (Hayashi et al.).
J. Pharm. Soc. Jap 1967, 87 164 (Ijima).
J. Pharm. Soc. Jap. 1962, 82, 1093 (Hayashi et al).

*Primary Examiner*—Alan L. Rotman
*Attorney, Agent, or Firm*—Gary L. Griswold; Walter N. Kirn; Douglas E. Reedich

[57] ABSTRACT

A process and intermediates for preparing 1-substituted-1H-imidazo[4,5-c]quinolin-4-amines. The process involves reacting a 1-substituted-1H-imidazo[4,5-c]quinoline-5N-oxide with an isocyanate and hydrolysing the product thereof. Also, a process for preparing the intermediates is disclosed.

10 Claims, No Drawings

IMIDAZO[4,5-C]QUINOLIN-4-AMINES AND PROCESSES FOR THEIR PREPARATION

BACKGROUND OF THE INVENTION

1. Field of the Invention

This invention relates to processes and intermediates for preparing 1H-imidazo[4,5-c]quinolines. In another aspect this invention relates to processes and intermediates for preparing 1-substituted-1H-imidazo[4,5-c]quinolin-4-amines.

2. Description of the Related Art

The synthesis of 1H-imidazo[4,5-c]quinolin-4-amines has been described in U.S. Pat. Nos. 4,689,338 (Gerster) and U.S. Pat. No. 4,929,624 (Gerster et al.). The methods described therein involve the step of heating the 4-chloro compound in the presence of ammonium hydroxide or ammonia under pressure (e.g., in a sealed reactor) to afford the 4-amino compound.

The reaction of phenyl isocyanate with heteroaromatic 6-membered ring N-oxides has been reported in "Organic Chemistry: A series of Monographs, Chemistry of the Heterocyclic N-oxides." A. R. Katritsky and J. Kagowski. Alfred T. Bloomquist, Ed., Academic Press, 1971. The reaction is said to afford the α-anilino derivative.

SUMMARY OF THE INVENTION

This invention provides a process for preparing a 1H-imidazo[4,5-c]quinolin-4-amino, comprising the steps of:

(i) providing a 1H-imidazo[4,5-c]quinoline 5N-oxide having no functional groups other than the 5N-oxide that are reactive to organic isocyanates;

(ii) reacting the 1H-imidazo[4,5-c]quinoline N-oxide from step (i) with an organic isocyanate of the formula $R_1$—X—NCO, wherein $R_i$ is an organic group substantially inert to quinoline N-oxides and X is a hydrolytically active functional group, to afford a 1H-imidazo[4,5-c]quinoline having a 4-substituent of the formula $R_i$—X—NH—;

(iii) hydrolysing the product of step (ii) to afford a 1H-imidazo[4,5-c]quinolin-4-amine; and (iv) isolating the product of step (iii) or a pharmaceutically acceptable acid-addition salt thereof.

This invention also provides a process for preparing a compound of Formula I

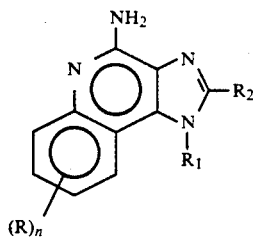

wherein $R_1$ is selected from the group consisting of: straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms;

$R_2$ is selected from the group consisting of hydrogen; straight chain or branched chain alkyl containing one to about eight carbon atoms; benzyl; (phenyl)ethyl; and phenyl; the benzyl, (phenyl)ethyl, or phenyl substituent being optionally substituted on the benzene ring by one or two moieties independently selected from the group consisting of lower alkyl, lower alkoxy, halogen, and

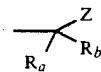

wherein $R_a$ and $R_b$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen; and Z is selected from the group consisting of alkoxy containing one to about four carbon atoms, alkylamido wherein the alkyl group contains one to about four carbon atoms, amino, substituted amino wherein the substituent is alkyl or hydroxyalkyl of one to about four carbon atoms, azido, chloro, hydroxy, 1-morpholino, 1-pyrrolidino, and thioalkyl of one to about four carbon atoms;

R is selected from the group consisting of lower alkoxy, halogen, and lower alkyl; and n is zero or one; or a pharmaceutically acceptable acid addition salt thereof, which process comprises the steps of:

(i) providing a compound of Formula II

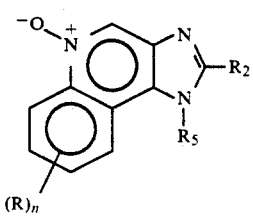

wherein R, n, and $R_2$ are as defined above with the proviso that Z in $R_2$ is other than amino, substituted amino, or hydroxy, and $R_5$ is selected from the group consisting of: straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or aroyloxy, and the alkyl moiety contains one to about six carbon atoms; benzyl; (phenyl)ethyl; and phenyl; said benzyl, (phenyl)ethyl, or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms;

(ii) reacting the compound of Formula II with an isocyanate of the formula $R_i$—X—NCO, wherein X is a hydrolytically active functional group and $R_i$ is an organic group substantially inert to quinoline N-oxides to afford an intermediate of Formula III

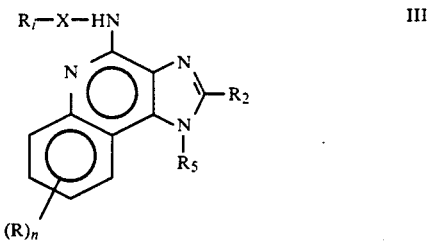

wherein X, $R_i$, R, $R_2$, $R_5$, and n are as defined above with the proviso that Z in $R_2$ is other than amino, substituted amino, or hydroxy;

(iii) hydrolysing the product of step (ii) to provide a compound of Formula I;

(iv) optionally converting or further elaborating the group Z in $R_2$; and (v) isolating the compound of Formula I from step (iv) or a pharmaceutically acceptable acid addition salt thereof.

This invention also provides intermediate compounds of Formula III above and a process for preparing such intermediates.

The processes of this invention allow an N-oxide of Formula II to be aminated directly without chlorination and subsequent use of the high pressure conditions used in previous syntheses of imidazo[4,5-c]quinolin-4-amines.

DETAILED DESCRIPTION OF THE INVENTION

For the purpose of the instant specification and claims, the term "lower" when used in connection with "alkyl" or "alkoxy" designates straight chain or branched chain groups containing one to about four carbon atoms.

The process of this invention is illustrated in the Reaction Scheme below, wherein X, $R_i$, R, n, $R_1$, $R_2$, and $R_5$ are as defined above.

Reaction Scheme

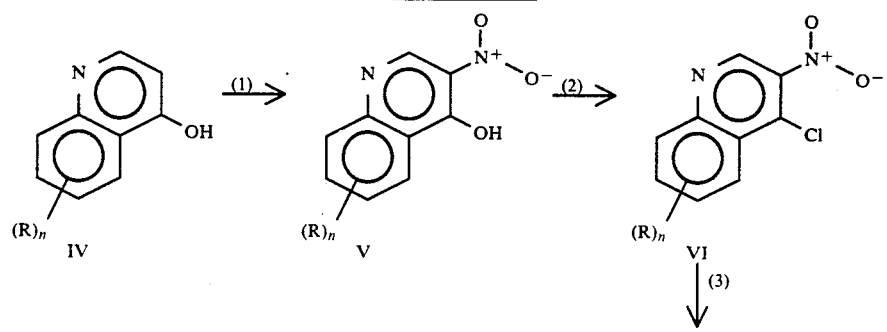

-continued
Reaction Scheme

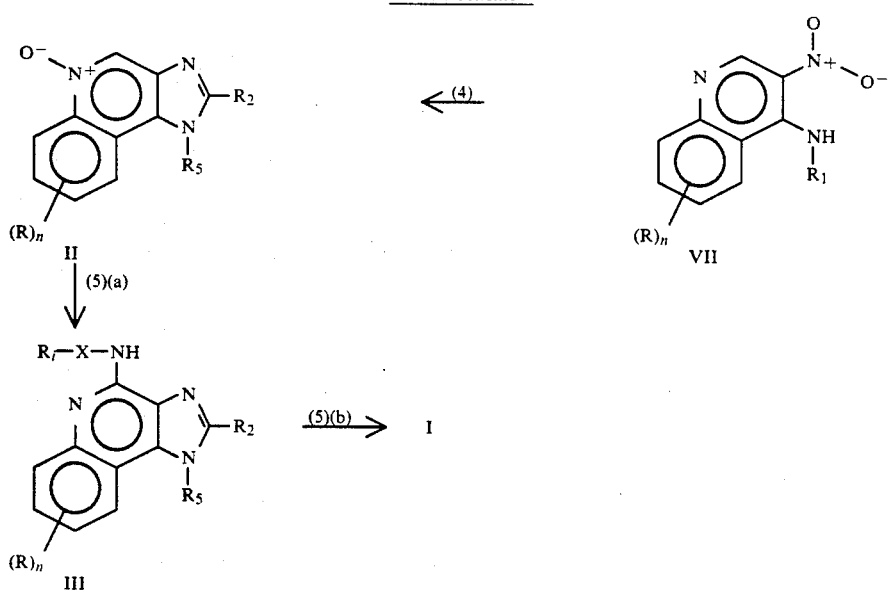

The Reaction Scheme begins with a 4-hydroxyquinoline of Formula IV. Many 4-hydroxyquinolines of Formula IV are commercially available. The others are known and/or can be prepared readily by those skilled in the art. Step 1 involves nitration of a 4-hydroxyquinoline to provide a 3-nitro-4-hydroxyquinoline of Formula V. Conventional conditions for such reactions are well known. Preferred conditions in the instance where n is zero, which afford a product of Formula V in superior yield compared with conditions used in the prior art, involve heating at about 125° C.–130° C. in propionic acid in the presence of nitric acid. Preferred conditions in other instances will depend upon the particular 4-hydroxyquinoline used in step 1, and those skilled in the art will be able to select suitable conditions.

In step 2, a 3-nitro-4-hydroxyquinoline is chlorinated at the 4-position to provide a 3-nitro-4chloroquinoline of Formula VI. Some compounds of Formula VI are known and disclosed, e.g., in U.S. Pat. No. 3,700,674 (Diehl et al.) and references cited therein, and U.S. Pat. No. 4,689,338 (Gerster), both patents being incorporated herein by reference. The others can be prepared as shown in step 2. Step 2 can be carried out by reacting a compound of Formula V in an inert solvent (e.g., methylene chloride) with a chlorinating agent (e.g., phosphorus oxychloride). Preferred conditions involve chlorination in methylene chloride with a Vilsmeier reagent prepared from thionyl chloride and N,N-dimethylformamide. In such a reaction, the compound of Formula V is suspended in methylene chloride, and a slight molar excess of thionyl chloride and N,N-dimethylformamide is added to the suspension. Heating to reflux facilitates the chlorination.

Step 3 involves reacting a compound of Formula VI in an inert solvent with an amine of the formula $R_1NH_2$ to provide a compound of Formula VII. Some compounds of Formula VII are disclosed in U.S. Pat. No. 4,689,338 (Gerster). The others can be prepared as shown in step 3. The reaction of step 3 is preferably carried out in the presence of a tertiary amine catalyst (such as triethylamine), and it is preferred to run the reaction without isolation of the chloro compound from step 2.

Step 4 involves several reactions including: (i) reduction of the nitro group of the compound of Formula VII, and (ii) reaction of the resulting 3-amino compound with a carboxylic acid or an equivalent thereof in order to provide a cyclized imidazo[4,5-c]quinoline.

The reduction in step (4) is preferably carried out using a conventional heterogeneous hydrogenation catalyst such as platinum on carbon. The reduction can be carried out conveniently on a Paar apparatus in an inert solvent such as toluene, ethyl acetate, or a lower alkanol.

In part (ii) of step 4, a 3-amino compound is reacted with (a) a 1,1-dialkoxyalkyl alkanoate such as diethoxymethyl acetate, or (b) a carboxylic acid that will introduce the desired $R_2$ group, or (c) a trialkyl ortho ester of the formula $R_2C(Oalkyl)_3$, wherein "alkyl" is an alkyl group containing one to about four carbon atoms, or (d) a combination of such a carboxylic acid with such a trialkyl ortho ester to provide an imidazo[4,5-c]-quinoline. The reaction can be carried out by heating, e.g., at about 130° C., in the presence of an acid, preferably an alkanoic acid having one more carbon atom than $R_2$.

An alternative to part (ii) of step 4 involves a reaction similar to that described above but involving formic acid or a trialkylorthoformate to form a 2-hydrogen substituted intermediate 1H-imidazo[4,5-c]quinoline. This compound is then deprotonated at the 2-position by a strong base (e.g., an alkyllithium such as n-butyllithium) and reacted with a compound of the formula

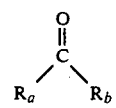

In instances wherein a primary or secondary hydroxyl group is present in the cyclized compound, part (ii) of step 4 also involves protecting the hydroxyl group with a removable protecting group such as an alkanoyloxy group (e.g., acetoxy) or an aroyloxy group (e.g., benzoyloxy). The protecting group can later be removed as appropriate when it will no longer interfere with subsequent reactions. Suitable protecting groups and reactions for their placement and removal are well known to those skilled in the art. See, for example, U.S. Pat. No. 4,689,338 (Gerster), Examples 115-123.

Part (iii) of step (4) provides an intermediate of Formula II. The quinoline nitrogen is oxidized with a conventional oxidizing agent that is capable of forming N-oxides. Preferred oxidizing agents include peroxyacids (such as peroxyacetic acid) and hydrogen peroxide. Preferred conditions involve mild heating (e.g., at about 50° C.–60° C.) in an ethanolic solution of peroxyacetic acid.

Some compounds of Formula II are disclosed in U.S. Pat. Nos. 4,689,338 and 4,698,348 (Gerster). The others can be prepared as described in connection with step 4 herein.

A 1H-imidazo[4,5-c]quinolin-4-amine is prepared in step (5) of the Reaction Scheme. Step (5) involves: (a) reacting a compound of Formula II with an isocyanate to afford an intermediate of Formula III; (b) hydrolysing the intermediate; (c) optionally converting or further elaborating the group Z in $R_2$; and (d) isolating the compound of Formula I from step (d) or a pharmaceutically acceptable acid addition salt thereof.

Part (a) of step (5) involves reacting an N-oxide with an isocyanate wherein the isocyanato group is bonded to a hydrolytically active functional group. The term "hydrolytically active functional group" as used herein designates any functional group that is capable of being subjected to a nucleophilic displacement reaction in step (5)(b) of the Reaction Scheme Exemplary hydrolytically active functional groups include carbonyl

A particular class of such isocyanates is isocyanates of the formula $R_i$—X—NCO, wherein $R_i$ is an organic group substantially inert to quinoline N-oxides under the conditions of step (5)(a) and X is a hydrolytically active functional group. Suitable $R_i$ groups are easily selected by those skilled in the art. Preferred groups $R_i$ include alkyl, aryl, alkenyl, and combinations thereof. Particular preferred isocyanates include aroyl isocyanates such as benzoylisocyanate. The reaction of the isocyanate with the N-oxide is carried out under substantially anhydrous conditions by adding the isocyanate to a solution of the N-oxide in an inert solvent such as dichloromethane. The resulting 4-substituted compound of Formula III can be isolated by removal of the solvent.

Step (5)(b) of the Reaction Scheme involves hydrolysis of a compound of Formula III. The term "hydrolysis" as used herein designates not only nucleophilic displacement with water but also displacement with other nucleophilic compounds. Such a reaction can be carried out by general methods well known to those skilled in the art, e.g., by heating in the presence of a nucleophilic solvent such as water or a lower alkanol optionally in the presence of a catalyst such as an alkali metal hydroxide or lower alkoxide.

In instances wherein there are hydroxyl protecting groups present in the compound of Formula III, they too can be removed in step (5)(b). A hydroxyl-containing compound of Formula I can be converted or further elaborated by methods well known to those skilled in the art to afford a further compound of Formula I. For example, reaction with thionyl chloride will provide a compound of Formula I wherein Z is chloro. Reaction of this compound with a nucleophile such as sodium azide, pyrrolidine, methanethiol, or morpholine will afford a compound of Formula I wherein Z is azido, 1-pyrrolidino, thiomethyl, or 1-morpholino, respectively. Reduction of an azido compound provides a compound of Formula I wherein Z is amino. Such an amino compound can be acylated to form a compound wherein Z is alkylamido.

Some compounds of Formula I can be prepared by a similar reaction scheme wherein the final desired group Z is introduced directly in step (4) and carried on through the process of the invention.

The product compound of Formula I can be isolated by the conventional means disclosed in U.S. Pat. No. 4,689,338 (Gerster), such as, for example, removal of the solvent and recrystallization from an appropriate solvent (e.g., N,N-dimethylformamide) or solvent mixture, or by dissolution in an appropriate solvent (e.g., methanol) and re-precipitation by addition of a second solvent in which the compound is insoluble.

The compounds of Formula I can be used in the form of acid addition salts such as hydrochlorides, dihydrogen sulfates, trihydrogen phosphates, hydrogen nitrates, methane sulfonates and salts of other pharmaceutically acceptable acids. Pharmaceutically acceptable acid-addition salts of compounds of Formula I are generally prepared by reaction of the respective compound with an equimolar amount of a relatively strong acid, preferably an inorganic acid such as hydrochloric, sulfuric or phosphoric acid or an organic acid such as methanesulfonic acid in a polar solvent. Isolation of the salt is facilitated by the addition of a solvent in which the salt is insoluble (e.g., diethyl ether).

Some of the 1H-imidazo[4,5-c]quinolin-4-amines prepared by the process of this invention are disclosed in U.S. Pat. Nos. 4,689,338 (Gerster) and 4,929,624 (Gerster et al.) as antiviral agents. The process as described above is illustrated in Example 1 below for the synthesis of 1-(2-methylpropyl)-1H-imidazo[4,5-c]quinolin-4-amine. The exemplified process affords the final product in a 40% overall yield from 4-hydroxyquinoline.

In the following Examples, all reactions were run with stirring under an atmosphere of dry nitrogen unless otherwise indicated. The particular materials and amounts thereof recited in the Example, as well as other conditions and details, should not be construed to unduly limit the invention.

EXAMPLE 1

1-(2-methylpropyl)-1H-imidazo[4,5-c]quinolin-4-amine

Part A

4-Hydroxyquinoline (26.2 g, 0.18 mol) was added to propionic acid (250 mL) and the solution was heated to about 125° C. Nitric acid (16.0 mL of a 70 percent aqueous solution, 0.36 mol) was added dropwise with stirring. When the addition was complete, the mixture was stirred at about 125° C. for 10 minutes, then allowed to cool to room temperature. The mixture was diluted with ethanol. The precipitated solid was filtered, washed sequentially with ethanol, water, and ethanol, and dried to afford 3-nitro-4-hydroxyquinoline (27.7 g, 86%) as a light yellow powder.

Part B

The compound 3-nitro-4-hydroxyquinoline (19.0 g, 0.10 mol) was suspended in dichloromethane (200 mL). Thionyl chloride (8.1 mL, 0.11 mol) and N,N-dimethylformamide (8.5 mL, 0.11 mol) were added. The reaction mixture was then heated for 3.5 hours at reflux, during which time a small amount of solid precipitated. The reaction mixture was then cooled to −15° C. and a solution of isobutylamine (15.1 mL, 0.15 mol), and triethylamine (20.9 mL, 0.15 mol) in dichloromethane (100 mL) was added in a slow stream with vigorous swirling. During the addition the temperature of the reaction mixture rose to 20° C. The resulting solution was heated at reflux for 30 minutes, cooled, and the solvent was removed at reduced pressure to afford a yellow solid product. The product was slurried in water, filtered, washed with water, and dried partially. The partially dried product was then slurried in ethanol (75 mL), filtered, washed successively with a small amount of ethanol and a small amount of diethyl ether, and dried at reduced pressure to afford a yellow crystalline solid product. A second crop of product was obtained by evaporating the ethanol filtrate. The total amount of N-(2-methylpropyl)-3-nitro-4-quinolinamine was 23.3 g.

Part C

N-(2-methylpropyl)-3-nitro-4-quinolinamine (61.3 g, 0.25 mol) was placed in a Paar apparatus along with 5% Pt/C (1.5 g), magnesium sulfate (60 g), ethyl acetate (750 mL), and formic acid (400 mL). The mixture was placed under a hydrogen atmosphere (about 50 psi) and hydrogenated. The catalyst was removed by filtration and the solvent was evaporated to afford the crude product. The crude product was dissolved in 98% formic acid (400 mL) and refluxed for 1 hour. The resulting solution was evaporated to dryness and the resulting solid was dissolved in ethanol (400 mL). Peroxyacetic acid (63 mL of an acetic acid solution containing 32% peroxyacetic acid based on the total weight of the solution, 0.3 mol) was added and the solution was heated at 56° C. for about 0.5 hour. The solution was then cooled and the solvents were removed at reduced pressure. The residue was then co-evaporated with heptane (3×300 mL) to afford a solid with spectral properties identical to those of an authentic sample of 1-(2-methylpropyl)imidazo[4,5-c]quinoline-5N-oxide.

Part D 1-(2-Methylpropyl)-1H-imidazo-[4,5-c]quinoline-5N-oxide (7.3 g, 0.0303 mol) was dissolved in dichloromethane (250 mL) and benzoyl isocyanate (5.0 g, 0.0306 mol) was dissolved in dichloromethane and added to the stirred solution. The reaction solution warmed spontaneously and refluxed briefly. The solution was then refluxed on the steam bath for 15 min and diluted with hexane until turbid. A crystalline solid formed and was filtered from the mixture, washed with dichloromethane/hexane, and dried. A yield of 8.1 g of colorless crystalline solid was obtained. A second crop of 1.4 g was obtained from the filtrate. A combined yield of 9.5 g of N-benzoyl-1-(2-methylpropyl)-1H-imidazo[4,5-c]quinolin-4-amine (91.1%) was obtained. Melting point 193° C.–196° C..

| Analysis | Calc'd | Found |
|---|---|---|
| C | 73.23% | % C: 73.29 |
| H | 5.85% | % H: 5.8 |
| N | 16.27% | % N: 16.3 |

Part E

N-Benzoyl-1-(2-methylpropyl)-1H-imidazol[4,5-c]quinolin-4-amine (5.0 g, 0.0145 mol) and sodium methoxide (10 drops of a 25% by weight solution in methanol) were mixed in methanol (50 mL) and the mixture was heated at reflux for 75 minutes. The mixture was cooled to room temperature, and a solid formed. The solid was filtered from the mixture, washed sequentially with water and methanol, and dried. A crude yield of colorless product of 3.3 g (94.3%) was obtained. Spectral properties of the product corresponded to those of an authentic sample.

EXAMPLE 2

4-Amino-1-(2-methylpropyl)α-phenyl-1H-imidazo[4,5-c]quinoline-2-methanol

Part A

3-Amino-4-(2-methylpropylamino)quinoline (43.5 g; 0.20 mole) and 300 mL of formic acid were combined and heated on a steam bath for several hours. The reaction mixture was concentrated under vacuum, diluted with water, basified with ammonium hydroxide then extracted twice with ether. The ether extracts were treated with activated charcoal then combined for a total volume of 1200 mL. The volume was reduced to 500 mL, cooled, then filtered to provide 31.1 g of a light green crystalline solid 1-(2-methylpropyl)-1H-imidazo[4,5-c]quinoline.

1-(2-Methylpropyl)-1H-imidazo[4,5-c]quinoline (4 g; 0.017 mole) was dissolved in 50 mL of tetrahydrofuran then cooled to −78° C. A 7.75 mL portion of n-butyl lithium (2.5M in hexanes) was added dropwise to the cooled solution. At 15 minutes post addition, benzaldehyde (2.7 mL; 0.027 mole) was added and the reaction mixture was allowed to warm slightly. The reaction was quenched with water then diluted with ethyl ether. The ether was separated, dried with magnesium sulfate then concentrated under vacuum. The resulting residue was purified by silica gel chromatography using 5% methanol in methylene chloride as the eluent to give an oily yellow solid. This material was recrystallized from methylene chloride/hexane to provide 1-(2-Methylpropyl)-α-phenyl-1H-imidazo[4,5-c]quinoline-2-methanol as a white crystalline solid, m.p. 160°–166° C. Analysis: Calc'd: C, 76.1; H, 6.4; N, 12.7; Found: C, 75.9; H, 6.3; N, 12.7.

Part B 1-(2-Methylpropyl)-α-phenyl-1H-imidazo[4,5-c]-quinoline-2-methanol (3 g; 9 mmole) was dissolved in 50 mL of methylene chloride then combined with acetic anhydride (1.3 mL; 13.5 mmole) and triethylamine (1.6 mL; 11.8 mole) and stirred at room temperature overnight. The reaction mixture was diluted with methylene chloride, washed sequentially with water and saturated sodium bicarbonate solution, dried over magnesium sulfate and concentrated under vacuum. The resulting residue was purified by silica gel flash chromatography (50% ethyl acetate in methylene chloride as eluent) to provide 1-(2-methylpropyl)-α-phenyl-1H-imidazo[4,5- c]quinoline-2-methyl acetate as a white solid. The structure was confirmed by nuclear magnetic resonance spectroscopy.

Part C 1-(2-Methylpropyl)-α-phenyl-1H-imidazo[4,5-c]quinoline-2-methyl acetate (3 g; 8 mmole) was dissolved in 50 mL of ethyl acetate then combined with peracetic acid (2.2 g; 8.8 mmole) and heated at reflux for about an hour. The reaction mixture was allowed to cool and then was stirred at room temperature for several days. The resulting precipitate was collected, rinsed with ethyl acetate and dried to provide 2.6 g of 2-(α-acetoxybenzyl)-1-(2-methylpropyl)-1H-imidazo[4,5-c]quinoline 5N oxide as a solid. The structure was confirmed by nuclear magnetic resonance spectroscopy.

Part D 2-(α-Acetoxybenzyl)-1-(2-methylpropyl)-1H-imidazo[4,5-c]quinoline 5N oxide (2.6 g; 6.7 mmole) was dissolved in about 40 mL of methylene chloride, combined with benzoyl isocyanate (1.2 g; 7.3 mmole) and heated at reflux for about one hour. The reaction mixture was diluted with methylene chloride, washed with water, dried over magnesium sulfate and concentrated under vacuum. The residue was taken up in methanol, combined with a catalytic amount of 25% sodium methoxide in methanol, and heated at reflux for several hours. The reaction product was purified by silica gel chromatography using 2-5% methanol in methylene chloride then recrystallized from ethyl acetate-hexane. The recrystallized material was co-evaporated twice with methylene chloride to provide about 0.5 g of 4-amino-1-(2-methylpropyl)-α-phenyl-1H-imidazo[4,5-c]quinoline-2-methanol as a solid, m.p. 125°-140° C. Analysis: Calc'd: C, 72.8; H, 6.4; N, 16.2; Found: C, 71.9; H, 5.6; N, 15.6.

EXAMPLE 3

4-Amino-α-(4-chlorophenyl)-1-(2-methylpropyl)-1H-imidazo[4,5-c]quinoline-2-methanol

Part A

Using the method of Example 2, Part A, 2.5 g of 1-(2-methylpropyl)-1H-imidazo[4,5-c]quinoline was reacted with 4-chlorobenzaldehyde to provide 3.1 g of α-(4-chlorophenyl)-1-(2-methylpropyl)-1H-imidazo[4,5-c]quinoline-2-methanol as a yellow solid. The structure was confirmed by nuclear magnetic resonance spectroscopy.

Part B

Using the method of Example 2, Part B, 2.6 g (7.1 mmole) of α-(4-chlorophenyl)-1H-imidazo[4,5-c]quinoline-2-methanol was reacted with acetic anhydride to provide α-(4-chlorophenyl)-1-(2-methylpropyl)-1H-imidazo[4,5-c]quinoline-2-methyl acetate as a thick oil. The structure was confirmed by nuclear magnetic resonance spectroscopy.

Part C

Using the method of Example 2, Part C, 2.9 g (7.1 mmole) of α-(4-chlorophenyl)-1-(2-methylpropyl)-1H-imidazo[4,5-c]quinoline-2-methyl acetate was oxidized with peracetic acid to provide 2-(α-acetoxy-4-chlorobenzyl)-1-(2-methylpropyl)-1H-imidazo[4,5-c]quinoline 5N oxide as an oil.

Part D

Using the method of Example 2, Part D, 3.3 g (7.8 mmole) of 2-(α-acetoxy-4-chlorobenzyl)-1-(2-methylpropyl)-1H-imidazo[4,5-c]quinoline 5N oxide was reacted with benzoyl isocyanate then hydrolyzed to provide 0.8 g of 4-amino-α-(4-chlorophenyl)-1-(2-methylpropyl)-1H-imidazo[4,5-c]quinoline-2-methanol as a solid, m.p. 140°-145° C. Analysis: Calculated: C, 66.2; H, 5.6; N, 14.7; Found: C, 65.6; H, 5.5; N, 14.4.

I claim:

1. A process for preparing a 1H-imidazo-4,5-c]quinolin-4-amine, comprising the steps of:
   (i) providing a 1H-imidazo[4,5-c]quinoline 5N-oxide having no functional groups other than the 5N-oxide that are reactive to organic isocyanates;
   (ii) reacting the 1H-imidazo[4,5-c]quinoline 5N-oxide from step (i) with an organic isocyanate of the formula $R_i$—X—NCO, wherein $R_i$ is an organic group substantially inert to quinoline N-oxides and X is a hydrolytically active functional group, to afford a 1H-imidazo[4,5-c]quinoline having a 4-substituent of the formula $R_i$—X—NH—;
   (iii) hydrolysing the product of step (ii) to afford a 1H-imidazo[4,5-c]quinolin-4-amine; and
   (iv) isolating the product of step (iii) or a pharmaceutically acceptable acid-addition salt thereof.

2. A process according to claim 1 for preparing a compound of Formula I:

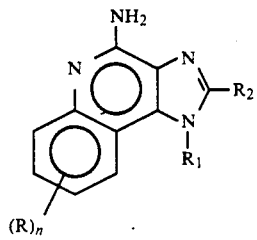

wherein
   $R_1$ is selected from the group consisting of: straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms;

$R_2$ is selected from the group consisting of hydrogen; straight chain or branched chain alkyl containing one to about eight carbon atoms; benzyl; (phenyl)ethyl; and phenyl; the benzyl, (phenyl)ethyl, or phenyl substituent being optionally substituted on the benzene ring by one or two moieties independently selected from the group consisting of lower alkyl, lower alkoxy, halogen, and

wherein $R_a$ and $R_b$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen; and Z is selected from the group consisting of alkoxy containing one to about four carbon atoms, alkylamido wherein the alkyl group contains one to about four carbon atoms, amino, substituted amino wherein the substituent is alkyl or hydroxyalkyl of one to about four carbon atoms, azido, chloro, hydroxy, 1-morpholino, 1-pyrrolidino, and thioalkyl of one to about four carbon atoms;

R is selected from the group consisting of lower alkoxy, halogen, and lower alkyl, and n is zero or one, or a pharmaceutically acceptable acid addition salt thereof, which process comprises the steps of:

(i) providing a compound of Formula II

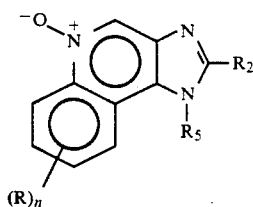

wherein R, n, and $R_2$ are as defined above with the proviso that Z in $R_2$ is other than amino, substituted amino, or hydroxy, and $R_5$ is selected from the group consisting of: straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or aroyloxy, and the alkyl moiety contains one to about six carbon atoms; benzyl; (phenyl)ethyl; and phenyl; said benzyl, (phenyl)ethyl, or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms;

(ii) reacting the compound of Formula II with an isocyanate of the formula $R_i$—X—NCO wherein X is a hydrolytically active functional group and $R_i$ is an organic group substantially inert to quinoline N-oxides to afford a compound of Formula III

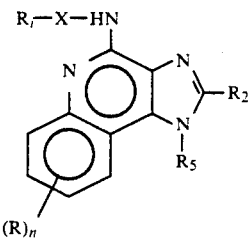

wherein X, $R_i$, R, $R_2 R_5$, and n are as defined above with the proviso that Z in $R_2$ is other than amino, substituted amino, and hydroxyl; and (iii) hydrolysing the product of step (ii) to provide a compound of Formula I;

(iv) optionally converting or further elaborating the group Z in $R_2$; and (v) isolating the compound of Formula I from step (iv) or a pharmaceutically acceptable acid addition salt therof.

3. A process according to claim 1, wherein X is

4. A process for preparing a compound of Formula I:

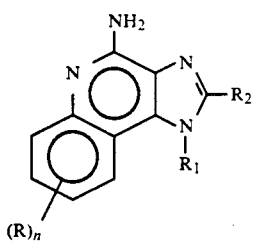

5. A process according to claim 1 wherein the compound is 1-(2-methylpropyl)-1H-imidazo[4,5-c]quinolin-4-amine.

6. A process according to claim 4, wherein X is

wherein
R$_i$ is selected from the group consisting of: straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms;

R$_2$ is selected from the group consisting of hydrogen; straight chain or branched chain alkyl containing one to about eight carbon atoms; benzyl; (phenyl)ethyl; and phenyl; the benzyl, (phenyl)ethyl, or phenyl substituent being optionally substituted on the benzene ring by one or two moieties independently selected from the group consisting of lower alkyl, lower alkoxy, halogen, and

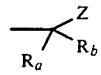

wherein R$_a$ and R$_b$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen; and Z is selected from the group consisting of alkoxy containing one to about four carbon atoms, alkylamido wherein the alkyl group contains one to about four carbon atoms, amino, substituted amino wherein the substituent is alkyl or hydroxyalkyl of one to about four carbon atoms, azido, chloro, hydroxy, 1-morpholino, 1-pyrrolidino, and thioalkyl of one to about four carbon atoms;

R is selected from the group consisting of lower alkoxy, halogen, and lower alkyl, and n is zero or one, or a pharmaceutically acceptable acid addition salt thereof, which process comprises the steps of:
(i) providing a compound of Formula III

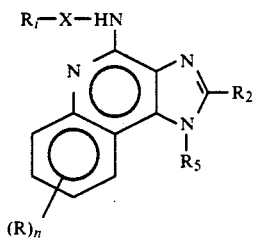

wherein X is a hydrolytically active functional group, R$_i$ is an organic group substantially inert to quinoline N-oxides, R, R$_2$, and n are as defined above with the proviso that Z in R$_2$ is other than amino, substituted amino, and hydroxyl, and R$_5$ is selected from the group consisting of: straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or aroyloxy, and the alkyl moiety contains one to about six carbon atoms; benzyl; (phenyl)ethyl; and phenyl; said benzyl, (phenyl)ethyl, or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms; and (ii) hydrolysing the compound of Formula III to provide a compound of Formula I;

(iii) optionally converting or further elaborating the group Z in $R_2$; and (iv) isolating the compound of Formula I from step (iii) or a pharmaceutically acceptable acid addition salt thereof.

7. A process for preparing a 1H-imidazo[4,5-c]quinoline having a 4-substituent of the formula $R_i$—X—NH—, wherein $R_i$ is an organic group substantially inert to quinoline N-oxides, and X is a hydrolytically active functional group, comprising the steps of:

(i) providing a 1H-imidazo[4,5-c]quinoline 5N-oxide having no functional groups other than the 5N-oxide that are reactive to organic isocyanates; and (ii) reacting the compound from step (i) with a compound of the formula $R_i$—X—NCO, wherein $R_i$ and X are as defined above.

8. A process according to claim 7 for preparing a compound of the formula

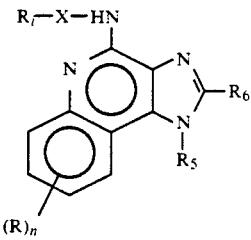

wherein $R_5$ is selected from the group consisting of: straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or aroyloxy, and the alkyl moiety contains one to about six carbon atoms; benzyl; (phenyl)ethyl; and phenyl; said benzyl, (phenyl)ethyl, or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms;

$R_6$ is selected from the group consisting of hydrogen; straight chain or branched chain alkyl containing one to about eight carbon atoms; benzyl; (phenyl)ethyl; and phenyl; the benzyl, (phenyl)ethyl, or phenyl substituent being optionally substituted on the benzene ring by one or two moieties independently selected from the group consisting of lower alkyl, lower alkoxy, halogen, and

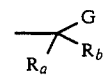

wherein $R_a$ and $R_b$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen; and G is selected from the group consisting of alkoxy containing one to about four carbon atoms, alkylamido wherein the alkyl group contains one to about four carbon atoms, azido, chloro, 1-morpholino, 1-pyrrolidino, and thioalkyl of one to about four carbon atoms;

R is selected from the group consisting of lower alkoxy, halogen, and lower alkyl, and n is zero or one;

X is a hydrolytically active functional group; and $R_i$ is an organic group substantially inert to quinoline N-oxides, comprising the steps of (i) providing a compound of Formula II

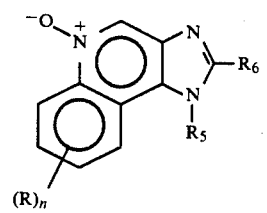

wherein R, n, $R_5$, and $R_6$ are as defined above;

(ii) reacting the compound of Formula II with an isocyanate of the formula $R_i$—X—NCO wherein X is a hydrolytically active functional group and $R_i$ is an organic group substantially inert to quinoline N-oxides.

9. A compound of the formula

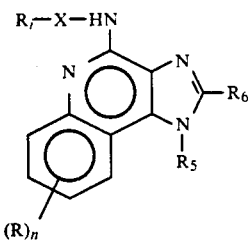

wherein X is a hydrolytically active functional group, $R_i$ is an organic group substantially inert to quinoline N-oxides, and wherein $R_5$ is selected from the group consisting of: straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or aroyloxy, and the alkyl moiety contains one to about six carbon atoms; benzyl; (phenyl)ethyl; and phenyl; said benzyl, (phenyl)ethyl, or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms;

$R_6$ is selected from the group consisting of hydrogen; straight chain or branched chain alkyl containing one to about eight carbon atoms; benzyl; (phenyl)ethyl; and phenyl; the benzyl, (phenyl)ethyl, or phenyl substituent being optionally substituted on the benzene ring by one or two moieties independently selected from the group consisting of lower alkyl, lower alkoxy, halogen, and

wherein $R_a$ and $R_b$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen; and G is selected from the group consisting of alkoxy containing one to about four carbon atoms, alkylamido wherein the alkyl group contains one to about four carbon atoms, azido, chloro, 1-morpholino, 1-pyrrolidino, and thioalkyl of one to about four carbon atoms;

R is selected from the group consisting of lower alkoxy, halogen, and lower alkyl; and n is zero or one.

10. A compound according to claim 9, wherein X is $$-\underset{\text{O}}{\overset{\|}{C}}-.$$

* * * * *

UNITED STATES PATENT AND TRADEMARK OFFICE
CERTIFICATE OF CORRECTION

PATENT NO. : 5,175,296
DATED : December 29, 1992
INVENTOR(S) : John F. Gerster

It is certified that error appears in the above-indentified patent and that said Letters Patent is hereby corrected as shown below:

Col. 15, lines 13-15, delete "5. A process according to claim 1 wherein the compound is 1-(2-methylpropyl)-1H-imidazo[4,5-c]quinolin-4-amine."

Col. 15, lines 16-20, delete "6. A process according to claim 4, wherein X is -C- ." 
O Col. 17, line 18, insert:

-- Claim 5. A process according to claim 1 wherein the compound is 1-(2-methylpropyl)-1H-imidazo[4,5-c]quinolin-4-amine.

Claim 6. A process according to claim 2, wherein X is -C- . -- 
O

Signed and Sealed this

Twenty-third Day of January, 1996

Attest:

BRUCE LEHMAN

*Attesting Officer*     *Commissioner of Patents and Trademarks*